United States Patent

He

[11] Patent Number: 5,972,945
[45] Date of Patent: Oct. 26, 1999

[54] 2-AMINOALKYLAMINOQUINOLINES; DOPAMINE RECEPTOR SUBTYPE SPECIFIC LIGANDS

[75] Inventor: Xiao-Shu He, Branford, Conn.

[73] Assignee: Neurogen Corporation, Branford, Conn.

[21] Appl. No.: 09/096,813

[22] Filed: Jun. 12, 1998

Related U.S. Application Data

[60] Provisional application No. 60/049,517, Jun. 13, 1997.

[51] Int. Cl.⁶ .................. A61K 31/495; A61K 31/505; C07D 401/14; C07D 401/12
[52] U.S. Cl. .................. 514/253; 514/312; 514/313; 544/295; 544/363; 546/153; 546/163
[58] Field of Search .................. 544/295, 363; 514/253

[56] References Cited

U.S. PATENT DOCUMENTS

| | | | |
|---|---|---|---|
| 4,590,273 | 5/1986 | Konz et al. | 544/363 |
| 4,605,642 | 8/1986 | Rivier | 514/12 |
| 5,063,245 | 11/1991 | Abreu | 514/404 |
| 5,093,333 | 3/1992 | Saab | 514/235.2 |
| 5,118,704 | 6/1992 | Minaskanian et al. | 514/416 |
| 5,314,885 | 5/1994 | Scott et al. | 514/252 |
| 5,372,813 | 12/1994 | Mathis, Jr. | 424/1.85 |
| 5,430,033 | 7/1995 | Cliffe et al. | 514/254 |
| 5,602,168 | 2/1997 | He et al. | 514/416 |
| 5,644,057 | 7/1997 | Yuan | 544/280 |
| 5,744,472 | 4/1998 | He et al. | 514/253 |
| 5,763,444 | 6/1998 | Smith et al. | 514/253 |

FOREIGN PATENT DOCUMENTS

| | | |
|---|---|---|
| 0 512 755 A2 | 11/1992 | European Pat. Off. |
| 0 512 755 B1 | 12/1994 | European Pat. Off. |
| S63-227570 | 9/1988 | Japan |
| WO 94/13676 | 6/1994 | WIPO |
| WO 94/20471 | 9/1994 | WIPO |
| WO 96/10018 | 4/1996 | WIPO |
| WO 96/39403 | 12/1996 | WIPO |

OTHER PUBLICATIONS

Terron et al., (1995), 1–Pharmacology, "Chemical Abstracts", vol. 122, No. 204541.

Zimmerman, et al., (1991), J. Am. Chem. Soc., "Synthesis and Structure of Molecular Tweezers Containing Active Site Functionality", 113: pp. 183–196.

Glennon, et al., (1986), J. Med. Chem., "5–HT₁ and 5–HT₂ Binding Characteristics of Some Quipazine Analogues", 29: pp. 2375–2380.

Terron, et al., (1994), Archives of Medical Research, "Pharmacological Screening of Some Quinoline Derivatives in Canine Vascular Smooth Muscle", 25: pp. 435–440.

Schmidt, et al., (1965), Toxicology and Applied Pharmacology, "The Effect of Diarylalkylpiperazines and Related Compounds on Plasma and Liver Lipids and Liver Size", 7: pp. 257–267.

Srivastava et al., Bioorganic & Medicinal Chemistry Letters, vol. 7, No. 21, pp. 2741–2746 Nov. 1997.

Van Tol et al., Nature, 350, 146 (1991).

Sokoloff et al., Nature, 347, 146 (1990).

Taubes, Science, 265, 1034 (1994).

Owens et al., Pharm. Rev., 43(4), 425–473 (1991).

Montgomery et al., J. Het. Chem., 9, 1077–1079 (1972).

Primary Examiner—Emily Bernhardt
Attorney, Agent, or Firm—McDonnell Boehnen Hulbert & Berghoff

[57] ABSTRACT

Disclosed are compounds of the formula:

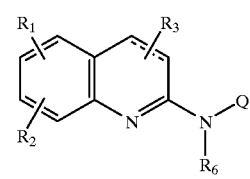

I or the pharmaceutically acceptable salts thereof wherein:

$R_1$, $R_2$, and $R_3$ are as defined herein;

$R_6$ is hydrogen or $C_1$–$C_6$ alkyl, and

Q represents a substituted azacycloalkylalkyl group, which compounds are useful in treating psychotic disorders such as schizophrenia and other central nervous system diseases.

22 Claims, No Drawings

2-AMINOALKYLAMINOQUINOLINES; DOPAMINE RECEPTOR SUBTYPE SPECIFIC LIGANDS

This application claims the benefit of U.S. Provisional Application Ser. No. 60/049,517 filed Jun. 13, 1997.

BACKGROUND OF THE INVENTION

1. Field of the invention

This invention relates to aminoquinoline derivatives which selectively bind to brain dopamine receptor subtypes. More specifically, it relates to 2-quinoly(azacycloalkylalkyl) amines and pharmaceutical compositions and preparations containing such compounds. It also relates to the use of such compounds in the treatment or prevention of neuropsychochological disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified. See Nature 350: 610 (Van Tol et al., 1991) and Nature, 347:146 (Sokoloff et al., 1990) Its unique localization in limbic brain areas and its differential recognition of various antipsychotics suggest that the $D_4$ receptor plays a role in the etiology of schizophrenia. Consequently, selective $D_4$ antagonists are considered effective antipsychotics free from the neurological side effects displayed by conventional neuroleptics.

U.S Pat. No. 5,093,333 describes N-substituted-2-aminoquinolines said to be $M_1$ receptor agonists.

SUMMARY OF THE INVENTION

This invention provides novel compounds of Formula I which interact with dopamine receptor subtypes. A broad aspect of the invention is directed to compounds of Formula I:

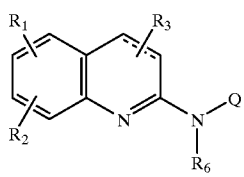

wherein:

$R_1$, $R_2$, and $R_3$ independently represent hydrogen, halogen, $C_1$–$C_6$ alkyl, $C_1$–$C_4$ alkoxy, $C_1$–$C_4$ alkylthio, hydroxy, amino, mono($C_1$–$C_6$) alkylamino, di($C_1$–$C_6$) alkylamino, cyano, nitro, trifluoromethyl or trifluoromethoxy;

$R_6$ is hydrogen or $C_1$–$C_6$ alkyl: and

Q represents a substituted azacycloalkylalkyl group of the formula:

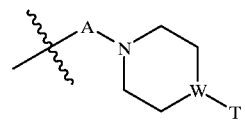

where

W is nitrogen, CH or COH,

A represents an alkylene group of from 2–5 carbon atoms optionally substituted with one or more alkyl groups having from one to four carbon atoms; and T is an aryl or heteroaryl moiety optionally substituted with up to two groups selected from hydrogen, halogen $C_1$–$C_6$ alkyl, $C_1$–$C_4$ alkoxy, $C_1$–$C_4$ alkylthio, hydroxy amino, mono($C_1$–$C_6$) alkylamino, di($C_1$–$C_6$) alkylamino, cyano, nitro, trifluoromethyl and trifluoromethoxy.

In yet another aspect, the invention provides pharmaceutical compositions comprising compounds of Formula I.

Since dopamine $D_4$ receptors are concentrated in the limbic system (Taubes, Science 265:1034, 1994) which controls cognition and emotion, compounds which interact with these receptors are useful in the treatment of cognitive disorders. Such disorders includes cognitive deficits which are a significant component of the negative symptoms (social withdrawal and unresponsiveness) of schizophrenia. In addition, disorders involving memory impairment or attention deficit disorders can be treated with the compounds of this invention. These compounds interact specifically with the dopamine $D_4$ receptor subtype.

The compounds of the invention demonstrate high affinity and selectivity in binding to the $D_4$ receptor subtype. The use of the compounds of this invention in methods of treating neuropsychlogical disorders is predicated on the ability of the compounds to bind selectively to a dopamine receptor subtype, the $D_4$ receptor. The compounds of the invention can therefore be used in the treatment of schizophrenia, psychotic depression and mania. Other dopamine-mediated diseases such as Parkinisonism and tardive dyskinesias can also be treated directly or indirectly by modulation of $D_4$ receptors.

Thus, in another aspect, the invention provides methods for treating and/or preventing neuropsychiological disorders including, for example, schizophrenia, mania, dementia, depression, anxiety, compulsive behavior, substance abuse, memory impairment, cognitive, deficits, Parkinson-like motor disorders and motion disorders related to the use of neuroleptic agents. It also provides methods of treating, affective disorders such as Alzheimer's disease and certain movements disorders such as Parkinsonism and dystonia.

The invention further provides methods for treating the extrapyramidal side effects associated with the use of conventional neuroleptic agents. The compounds of the present invention are also useful for the treatment of other disorders which respond to dopaminergic blockade such as substance abuse and obsessive compulsive disorder.

DETAILED DESCRIPTION OF THE INVENTION

In addition to the compounds of Formula I above, the invention encompasses compounds of Formula IA:

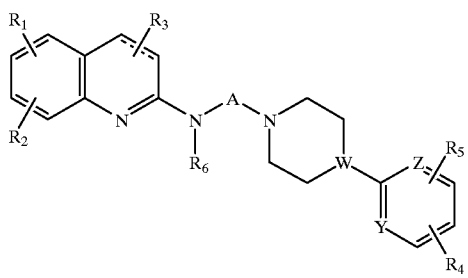

IA wherein:

R$_1$, R$_2$, R$_3$, R$_4$ and R$_5$ are the same or different and represent hydrogen, halogen, C$_1$–C$_6$ alkyl, C$_1$–C$_4$ alkoxy, C$_1$–C$_4$ alkylthio, hydroxy, amino, mono (C$_1$–C$_6$) alkylamino, di(C$_1$–C$_6$) alkylamino, cyano, nitro, trifluormethyl or trifluoromethoxy;

R$_6$ is hydrogen or C$_1$–C$_6$ alkyl;

W is nitrogen, COH, or CH;

Y and Z independently represent nitrogen or CH; and

A represents an alkylene group of from 2–5 carbon atoms optionally substituted with one or more alkyl groups having from one to four carbon atoms.

In Formula IA, the dashed segment represents either a single bond resulting in a 3,4 dihydroquinoline; or a double bond resulting in a quinoline.

In the compounds of the invention, "W" preferably represents nitrogen or COH. Preferred "T" groups in Formula I are 6-membered carbocyclic aromatic ring systems having zero, one or two nitrogen atoms. Particulary preferred "T" groups are phenyl, 2-pyridinyl, and 2-pyrimidinyl, The particularly preferred "T" groups are optionally mono- or disubstituted with halogen, C$_1$–C$_6$ alkyl, C$_1$–C$_4$ alkoxy, C$_1$–C$_4$ alkylthio, hydroxy, amino, mono(C$_1$–C$_6$) alkylamino, di(C$_1$–C$_6$) alkylamino, cyano, nitro, trifluoromethyl or trifluoromethoxy.

Preferred compounds of Formula IA are those where R$_6$ is hydrogen, methyl or ethyl.

Preferred "T" groups in Formula I are

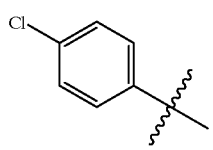

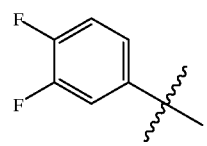

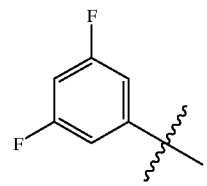

-continued

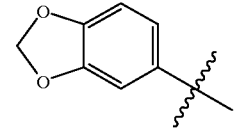

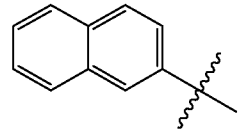

or

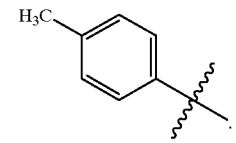

.

The invention also provides compounds of Formula II:

II wherein:

R$_1$, R$_2$, R$_3$, R$_4$ and R$_5$ are the same or different and represent hydrogen, halogen, C$_1$–C$_6$ alkyl, C$_1$–C$_4$ alkoxy, C$_1$–C$_4$ alkylthio, hydroxy, amino, mono (C$_1$–C$_6$) alkylamino, di(C$_1$–C$_6$) alkylamino, cyano, nitro, trifluoromethyl or trifluoromethoxy, R$_6$ is hydrogen or C$_1$–C$_6$ alkyl;

W is nitrogen, COH, or CH,

Y and Z independently represent nitrogen or CH, and

A represents an alkylene group of from 2–5 carbon atoms optionally substituted with one or more alkyl groups having from one to four carbon atoms.

Preferred compounds of Formula II are those where R$_6$ is hydrogen methyl or ethyl. Particularly preferred compounds of Formula II are those where In addition, the invention encompasses compounds of Formula III:

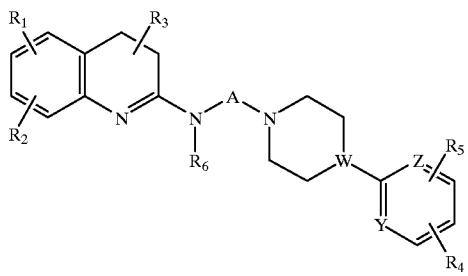

wherein:
R₁, R₂, R₃, R₄ and R₅ are the same or different and represent hydrogen, halogen, $C_1$–$C_6$ alkyl, $C_1$–$C_4$ alkoxy, $C_1$–$C_4$ alkylthio, hydroxy, amino, mono($C_1$–$C_6$) alkylamino, di($C_1$–$C_6$) alkylamino, cyano, nitro, trifluoromethyl or trifluoromethoxy;

R₆ is hydrogen or $C_1$–$C_6$ alkyl;

W is nitrogen, COH, or CH;

Y and Z independently represent nitrogen or CH; and

A represents an alkylene group of from 2–5 carbon atoms optionally substituted with one or more alkyl groups having from one to four carbon atoms.

In preferred compounds of Formula III, R₆ is hydrogen, methyl or ethyl.

In certain situations, compounds of Formula I may contain one or more asymmetric carbon atoms, so that the compounds can exist in different steroisomeric forms. These compounds can be, for example, racemates or optically active forms. For example, where R₆, in Formula I is a methyl group, the resulting compound can be present as (R) and (S) stereoisomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable salts. If the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenlesulfonic, methanesulfonic, nitric, benzoic, citric, tartaric, maleic, hydroiodic, alkanoic such as, for example, acetic, $HOOC—(CH_2)_n—COOH$ where n is 0–4, such as, for example, oxalic (n=0), and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By the terms ($C_1$–$C_6$)alkyl and lower alkyl is meant straight and branched chain alkyl groups having from 1–6 carbon atoms as well as cyclic alkyl, groups such as, for example, cyclopropyl, cyclobutyl, or cyclohexyl. Specific examples of such alkyl groups are methyl, ethyl, propyl, isopropyl, n-butyl, isobutyl, tert-butyl, sec-butyl, neopentyl and n-pentyl. Preferred $C_1$–$C_6$ alkyl groups are methyl, ethyl, propyl, butyl or cyclopropylmetyl.

By the terms ($C_1$–$C_6$)alkoxy and lower alkoxy is meant straight and branched chain alkoxy groups having from 1–6 carbon atoms.

By hydroxy $C_1$–$C_6$ alkyl is meant a $C_1$–$C_6$alkyl group carrying a terminal hydroxy moiety.

By halogen, halo, or halide is meant fluorine, chlorine, bromine and iodine substituents.

The binding characteristics of compounds of Formula I for the $D_4$ receptor, expressed in nM, generally range from about 0.5 nanomolar (nM) to about 50 nanomolar (nM). These compounds typically have binding constants for the $D_2$ receptor of from at least about 100 nM to more than 3000 nM. Thus, the compounds of the invention are generally at least about 3, preferably, at least about 5, and most preferably at least about 10 time more selective for the $D_4$ receptor than the $D_2$ receptor. Even more preferably, these compounds are at least 20, and more preferably at least 25–50, times more selective for the $D_4$ receptor than the $D_2$ receptor.

As noted above, the invention also pertains to the use of compounds of general Formula I in the treatment of neuropsychiological disorders.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition there is provided a pharmaceutical formulation comprising a compound of Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate, granulating and disintegrating agents, for example, corn starch, or alginic acid; binding agents, for example starch, gelatin or acacia, and lubricating, agents, for example maginesium stearate, stearic acid or talc. The tablets may be uncoated or they may be coated by known techniques to delay disintegration and absorption in the gastrointestinal tract and thereby provide a sustained action over a longer period. For example a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylecellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be fromulated by suspending the active ingredients in a vegetable oil, for example arachis oil, olive oil, sesame oil or coconut oil, or in a mineral oil such as liquid paraffin. The oily supensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the and partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including, synthetic mono or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending, on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage from will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing, therapy.

Preparation of 2-Aminoalkylaminoquinolines

The compounds of Formula I, and the pharmaceutically acceptable acid addition salts thereof, may be prepared according to the reactions shown below in Schemes I and II.

Scheme I

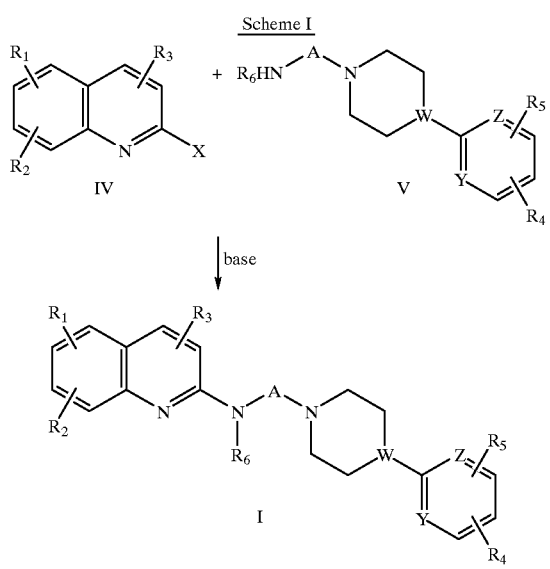

wherein $R_1$–$R_6$, W, Y and Z are as defined above for Formula I.

As shown in Scheme I, a quinoline of general structure IV, possessing an appropriate leaving group (X) at the 2 position e.g., a halogen or S-methyl group, may be reacted with a primary or secondary amine of general structure V in the presence of a base to afford a compound of Formula I as the desired product. The reaction may be carried out at elevated temperature with or without a solvent. Further, the reaction mixture may also contain an acid scavenger such as diisopropylamine or an inorganic salt such as ammonium chloride.

Where they are not commercially available, the compounds of general structure IV may be prepared by literature procedures or procedures analogous to those described in the literature. Compounds of general structure V are either known or capable of being prepared by the methods known in the art. Those having, skill in the art will recognize that the starting materials may be varied and additional steps employed to produce compounds encompassed by the present invention.

Alternatively, compounds of the invention may be prepared according to the reactions shown in Scheme II. Thus, compounds may be prepared from readily available substituted or unsubstituted 4-haloquinoline compounds by allowing them to react with a Wittig reagent, such as an alkyl triphenylphosphonate generated from an alkyltriphenylphosphonium halide, plus a base, such as n-butyllithium in an organic solvent, such as tetrahydrofuran. The resulting, 4-alkylquinoline can be converted to a 4-alkyl-2-haloquinoline by treatment with an oxidizing agent, such as m-chloroperbenizoic acid (MCPBA) in an appropriate solvent, such as chloroform, to give the corresponding 4-alkylquinoline N-oxide, followed by reaction with a halogenating agent, such as phosphorus oxychloride to give a 4-alkyl-2-haloquinoline of Formula IVa. Reaction of 2-haloquinoline IVa with amines of Formula V, as described above, yields compounds of this invention.

Scheme II

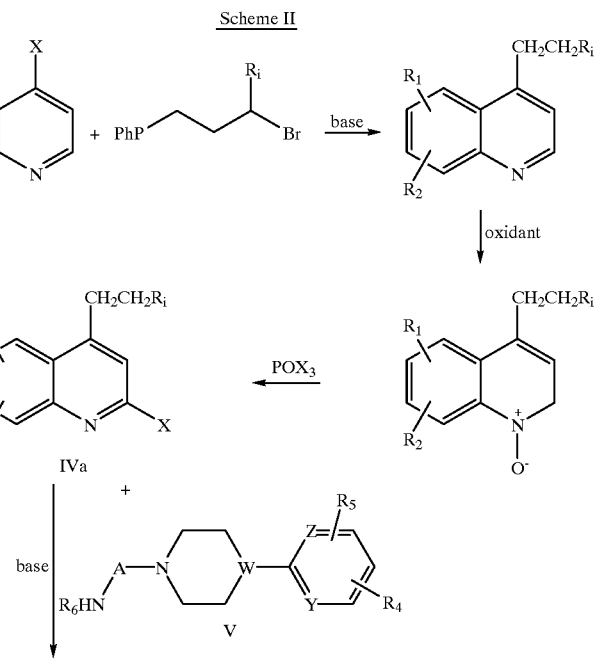

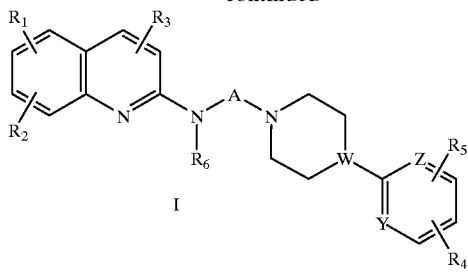

wherein $R_1$–$R_6$, are as defined above, $R_1$ is alkyl of 1 to 4 carbon atoms, and X is halogen.

The disclosures in this application of all articles and references including patents are incorporated herein by reference.

Those having skill in the art will recognize that the starting materials may be varied and additional steps employed to produce compounds encompassed by the present invention. The invention is illustrated further by the following examples which are not to be construed as limiting the invention in scope or spirit to the specific procedures and compounds described in them.

EXAMPLE 1
Preparation of 1-(Pyrimidin-2-yl)-4-(2-aminoethyl) piperazine

A mixture of N-(2-bromoethyl)phthalimide (50.8 g, 0.2 mole), 1-(pyrimidin -2-yl)piperazine (32.8 g, 0.2 mole) and potassium carbonate (55.2 g, 0.4 mole) in dimethyl formamide (400 mL) is heated at 80 °C. for 16 hours under a nitrogen atmosphere. After cooling, the reaction mixture is poured into water (1 L) and ether. (1 L). The heterogeneous mixture is then filtered to remove solids and the layers separated. The aqueous layer is further extracted with ether (2×300 ml). The combined organic layers are dried ($Na_2SO_4$) and concentrated to provide colorless crystals (65 g, 96%, m.p. 132–133° C.).

A portion of the crystals (5 g, 15 mole) is refluxed under nitrogen in hydrazine hydrate (50 mL) for 7 h. After cooling the solution is poured into 30% potassium carbonate solution (50 mL) and extracted with methylene chloride. The organic extracts are dried ($Na_2SO_4$) and concentrated to give a pale yellow oil (3.27 g). This oil is dissolved in methanol (5 mL) and combined with a methanolic solution (10 mL) of fumaric acid (3.66 g). Isopropanol is then added (50 mL) and the resulting mixture concentrated on hot plate to a volume of 20 mL. Upon cooling, the crystals of fumarate salt are collected (4.77 g. 99%, m.p. 260° C. dec)

EXAMPLE 2
Preparation of (2-(4-pyrimidin-2-ylpiperazinyl)ethyl)-2-quinolylamine (Compound 1)

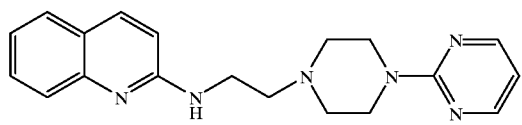

A solution of 1-(pyrimidin-2-yl)-4-(2-aminoethyl) piperazine (1 g) in xylene (200 mL) is treated with 2-chloroquinoline (1.5 g) and potassium carbonate (2 g). The mixture is then refluxed under $N_2$ overnight. After cooling the solution is diluted with diethyl ether (200 mL) and washed with water (3×50 mL). The organic layer is then extracted with an aqueous solution of 10% acetic acid. The aqueous extract is subsequently washed with ether (50 mL), basified with 50% NaOH solution and extracted with ether. The ether layer is dried ($K_2CO_3$) and evaporated to give the product as an oil (0.47 g). The oil is dissolved in ethanol (20 mL). treated with 48% HBr until acidic and concentrated to a volume of approx. 5 mL. Upon cooling, the off-white crystalline hydrobromide salt is collected by filtration (0.45 g, mp 174–176° C).

EXAMPLE 3
Preparation of 2-3,4-dihdroquinolyl(2-(4-(2-pyridyl) piperazinyl)ethyl)amine (Compound 2)

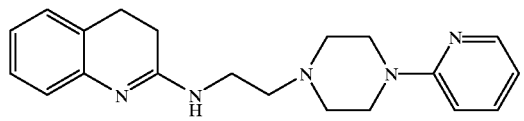

A solution of 3,4-dihydro-2(1H)-quinolinone (515 mg) and trimethyloxonium tetrafluoroborate (590 mg) in 50 mL of dry pentene stabilized chloroform is stirred at room temperature overnight. To this mixture is then added 1-(pyridin-2-yl)-4-(2-aminoethyl)piperazine (800 mg) and triethylamine (5 mL). The resultant solution is refluxed overnight under nitrogen. After cooling solution is concentrated and partitioned between water and ethyl acetate. The organic layer is dried and concentrated to give a brown oil. Purification using preparative thin layer chromatography on silica eluting with 10% $CH_3OH$, 89% $CHCl_3$, 1% $NH_4OH$ provides the product as a colorless oil (610 mg, $R_f$=0.51). This material is combined with 420 mg of fumaric acid in 5 mL of methanol. Isopropanol (20 mL) is added and the volume of solution reduced to approximately 5 mL on a hot plate. Upon cooling, the product (700 mg, m.p. 200–202° C.) is collected by filtration.

EXAMPLE 4
Preparation of 2-3,4-dihydroquinoly(2-(4-(5-fluoropyrimidin-2-yl)piperazinyl)ethyl)amine (Compound 3)

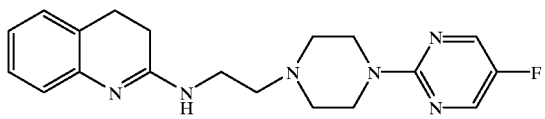

A solution of 3,4-dihydro-2(1H)-quinolinone (515 mg) and trimethyloxonium tetrafluoroborate (590 mg) in 50 mL of dry pentene stabilized chloroform is stirred at room temperature overnight. To this mixture is then added 1-(5-fluoropyrimidin-2-yl)-4-(2-aminoethyl)piperazine (650 mg) and triethylamine (5 mL). The resultant solution is refluxed overnight under nitrogen. After cooling the solution is concentrated and partitioned between water and ethyl acetate. The organic layer is dried and concentrated. Purification using preparative thin layer chromatography on silica eluting with 10% $CH_3OH$, 89% $CHCl_3$, 1% $NH_4OH$ affords the product as a yellow oil (410 mg, $R_f$=0.46). This material is combined with 270 mg of fumaric acid in 5 mL of methanol. Isopropanol (20 mL) is added and the solution reduced to a volume of approximately 5 mL on a hot plate. Upon cooling the product (349 mg, m.p. 170–171° C.) is collected by filtration.

EXAMPLE 5

The following compounds are prepared essentially according to the procedures set forth above in Examples 1 and 2.

(a) (2-(4-pyrimidin-2-ylpiperazinyl)ethyl)-2-quinolylamine hydrobromide (Compound 4, m.p. 174–176° C.)

(b) (3-(4-pyrimidin-2-ylpiperazinyl)propyl)-2-quinolylamine hydrobromide (Compound 5, m.p. 127–128° C.)

(c) (4-(4-pyrimidin-2-ylpiperazinyl)butyl)-2-quinolylamine hydrobromide (Compound 6, m.p. 274–276° C.)

(d) (3-(4-(2-methoxyphenyl)piperazinyl)propyl)-2-quinolylamine fumarate (Compound 7. m.p. 159–160° C.)

(e) (3-(4-(2-pyridyl)piperazinyl)propyl)-2-quinolylamine hydrobromide (Compound 8, m.p. 137–139° C.)

(f) (3-(4-phenylpiperazinyl)propyl)-2-quinolylamine hydrobromide (Compound 9, m.p. 228–229° C.)

(g) (3-(4-(2,3-dimethylphenyl)piperazinyl)propyl)-2-quinolylamine fumarate (Compound 10, m.p. 186–187° C.)

(h) (4-methyl(2-quinolyl))(2-(4-pyrimidin-2-ylpiperazinyl)ethyl)amine hydrobromide (Compound 11, m.p. >270° C.)

(i) (4-methyl(2quinolyl))(3-)4-pyrimidin-2ylpiperazinyl) propyl)amine hydrobromide (Compound 12, m.p. 255–260° C.)

(j) (4-methyl(2-quinolyl))(4-(4-pyrimidin-2-ylpiperazinyl)butyl)amine hydrobromide (Compound 13, m.p. >260° C.)

(k) (4-methyl(2-quinolyl))(3-(4-(2-methoxyphenyl) piperazinyl)propyl amine fumarate (Compound 14, m.p. 177–179° C.)

(l) (4-methyl(2-quinolyl))(3-(4-(2-pyridyl)piperazinyl) propyl)amine hydrobromide (Compound 15)

(m) (4-methyl(2-quinolyl))(3-(4-phenylpiperazinyl) propyl)amine fumarate (Compound 16, m.p. 208–209° C.)

(n) (4-methyl(2-quinolyl))(3-(4-(2,3-dimethylphenyl) piperazinyl)propyl)amine fumarate (Compound 17, m.p 159–160° C.)

(o) (2-(4-(5-fluoropyrimidin-2-yl)piperazinyl)ethyl)-2-quinolylamine hydrobromide (Compound 18. m.p. 150–151° C.)

(p) (4-methyl(2-quinolyl))(2-(4-(5-fluoropyrimidin-2-yl) piperazinyl)ethyl)amine hydrobromide (Compound 19, m.p. 250–253° C.)

(q) (4-(4-pyrimidin-2-ylpiperazinyl)butyl)-2-quinolylamine (compound 20)

(r) (3-(4-(2,3-dimethylphenyl)piperazinyl)propyl)2-quinolylamine (Compound 21)

(s) (4-methyl(2-quinolyl))(3-(4-(pyrimidin-2-yl) piperazinyl)propyl)amine (Compound 22)

EXAMPLE 6

The following compounds are prepared essentially according to the procedures set forth above in Examples 3 and 4.

(a) 2-3,4-dihydroquinolyl(2-(4-(pyrimidin-2-yl) piperazinyl)ethyl)amine fumarate (Compound 20, m.p. 217–218° C.)

(b) 2-3,4-dihydroquinolyl(3-(4-(pyrimidin-2-yl) piperazinyl)propyl)amine fumarate (Compound 21, m.p. 194–195° C.)

(c) 2-3,4-dihydroquinolyl(4-(4-(5-fluoropyrimidin-2-yl) piperazinyl)butyl)amine hydrobromide (Compound 22, m.p. 279–280° C., dec)

(d) 2-3,4-dihydroquinolyl(2-(4-(5-fluoropyrimidin-2-yl) piperazinyl)ethyl)amine fumarate (Compound 23, m.p. 200–201° C.)

(e) 2-3,4-dihydroquinolyl(3-(4-(5-fluoropyrimidin-2-yl) piperazinyl)propyl)amine fumarate (Compound 24, m.p. 173–176° C.)

(f) 2-3,4-dihydroquinolyl(4-(4-(5-fluoropyrimidin-2-yl) piperazinyl)butyl)amine fumarate (Compound 25, m.p. 182–183° C.)

(g) 2-3,4-dihydroquinolyl(4-(4-(5-methylpyrimidin-2-yl) piperazinyl)butyl)amine fumarate (Compound 26, m.p. 253–254° C.)

(h) 2-2,3-dihydroquinolyl(2-(4-(2-pyridyl)piperazinyl) ethyl)amine fumarate (Compound 27)

(i) 2-3,4-dihydroquinolyl(3-(4-(2-pyridyl)piperazinyl) propyl)amine fumarate (Compound 28, m.p. 190–191° C.)

(j) 2-3,4-dihydroquinolyl(4-(4-(2-pyridyl)piperazinyl) butyl)amine fumarate (Compound 29, 154–155° C.)

(k) 1-(3-(2-3,4-dihydroquinolylamino)propyl)-4-phenylpiperidin-4-ol hydrobromide (Compound 30, m.p. 247° C.)

Compound 30

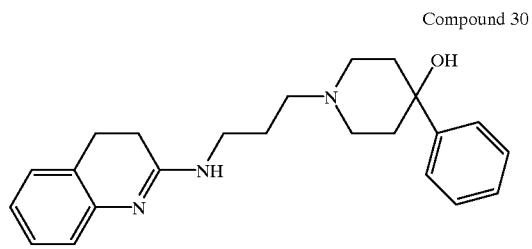

(1) 4-(4-chlorophenyl)-1-(3-(2-3,4-dihydroquinolylamino)propyl)piperidin-4-ol hydrobromide (Compound 31, m.p. >260° C.)

Compound 31

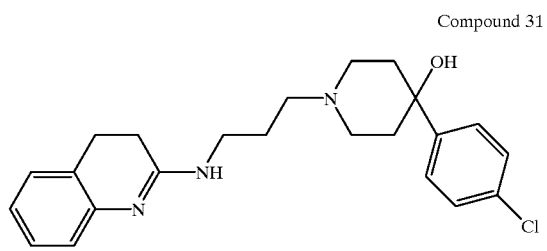

EXAMPLE 7

The pharmaceutical utility of compounds of this invention is indicated by the assays for dopamine receptor subtype affinity described below.

Representative examples of 2-aminoalkylaminoquinolines according to the invention and representative corresponding, biological acitvities are shown in Table 1 below. The number below each compound is its compound is its compound number. Each of these compounds may be prepared according to the reactions described above and shown in Scheme I.

Compounds 1–4 in Table 1 have the following formula A:

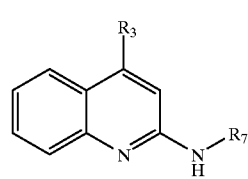

where $R_3$ and $R_7$ are defined in the table.

Compounds 5–6 in Table 1 have the following, general formula B:

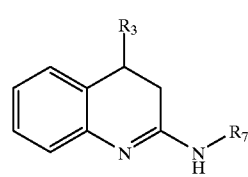

where $R_3$ and $R_7$ are defined in the table.

Assay for $D_2$ and $D_4$ Receptor Binding Activity

Pellets of COS cells containing recombinantly produced $D_2$ or $D_4$ receptors from African Green monkey were used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1mM spiperone; without further additions nonspecific binding is less than 20% of total binding. Binding characteristics of various compounds of the invention for $D_2$ and $D_4$ receptor subtypes are shown in Table 1 for rat striatal homogenates.

Various compounds of the invention were also evaluated in $M_1$ and $M_2$ Muscarinic subtype assays essentially as set forth in U.S. Pat. No. 5,093,333. The acitivity of the compounds is shown in Table 1.

TABLE 1

| Compound Number | $R_1$ | $R_7$ | $D_2$ $K_i$(nM) | $D_4$ $K_i$(nM) | $M_1$ (nM) | $M_2$ (nM) |
|---|---|---|---|---|---|---|
| 1 | H | (piperazinyl-pyrimidine group) | 2720 | 10 | 264 | 299 |
| 11 | CH$_3$ | (piperazinyl-pyrimidine group) | | 10 | 178 | 246 |

TABLE 1-continued

| Compound Number | R$_1$ | R$_7$ | D$_2$ K$_i$(nM) | D$_4$ K$_i$(nM) | M$_1$ (nM) | M$_2$ (nM) |
|---|---|---|---|---|---|---|
| 21 | H | –(CH$_2$)$_4$–N(piperazine)N–(2,3-dimethylphenyl) | >100 | 22 | | |
| 22 | CH$_3$ | –(CH$_2$)$_4$–N(piperazine)N–(pyrimidin-2-yl) | 3300 | 10 | | |
| 2 | H | –(CH$_2$)$_3$–N(piperazine)N–(pyridin-2-yl) | >100 | 30 | | |
| 3 | H | –(CH$_2$)$_3$–N(piperazine)N–(5-fluoropyrimidin-2-yl) | | 8 | 128 | 144 |

Various compounds disclosed in U.S. Pat. No. 5,093,333 (Saab) were evaluated in the D$_4$, M$_1$, and M$_2$ receptor assays as described above. The activity of these compounds is shown below in Table 2.

| Saab Example No. | Structure | M$_1$ | M$_2$ | D$_4$ |
|---|---|---|---|---|
| 1 | 4-methyl-2-[(3-morpholinopropyl)amino]quinoline | 1200 | 2500 | >1000 |
| 2 | 2-[(3-morpholinopropyl)amino]quinoline | 2500 | 11600 | >1000 |
| 3 | 4-methyl-2-{[3-(4-methylpiperazin-1-yl)propyl]amino}quinoline | 600 | 2800 | >1000 |
| 7 | 4-methyl-2-{[3-(2-oxopyrrolidin-1-yl)propyl]amino}quinoline | 1300 | 20000 | >1000 |

What is claimed is:

1. A compound of the formula:

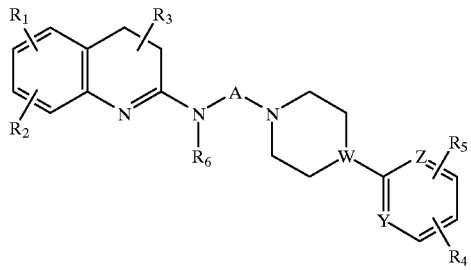

or the pharmaceutically acceptable acid addition salts thereof wherein:
$R_1$, $R_2$, $R_3$, $R_4$ and $R_5$ are the same or different and represent hydrogen, halogen, $C_1$–$C_6$ alkyl, $C_1$–$C_4$ alkoxy, $C_1$–$C_4$ alkylthio, hydroxy, amino, mono ($C_1$–$C_6$) alkylamino, di($C_1$–$C_6$) alkylamino, cyano, nitro, trifluoromethyl or trifluoromethoxy;
$R_6$ is hydrogen or $C_1$–$C_6$ alkyl;
W is nitrogen;
Y and Z independently represent nitrogen or CH; and
A represents an alkylene group of from 2–5 carbon atoms optionally substituted with one or more alkyl groups having from one to four carbon atoms.

2. A compound according to claim 1, wherein $R_6$ is hydrogen, methyl or ethyl.

3. A compound according to claim 1, which is 2-3,4-dihydroquinolyl(2-(4-(pyrimidin-2-yl)piperazinyl)ethyl amine fumarate.

4. A compound according to claim 1, which is 2-3,4-dihydroquinolyl(3-(4-(pyrimidin-2-yl)piperazinyl)propyl) amine fumarate.

5. A compound according to claim 1, which is 2-3,4-dihydroquinolyl(4-(4-(5-fluoropyrimidin-2-yl)piperazinyl)butyl)amine hydrobromide.

6. A compound according to claim 1, which is 2-3,4-dihydroquinolyl(2-(4-(5-fluoropyrimidin-2-yl)piperazinyl)ethyl)amine fumarate.

7. A compound according to claim 1, which is 2-3,4-dihydroquinolyl(3-(4-(5-fluoropyrimidin-2-yl)piperazinyl)propyl)amine fumarate.

8. A compound according to claim 1, which is 2-3,4-dihydroquinolyl(4-(4-(5-fluoropyrimidin-2-yl)piperazinyl)butyl)amine fumarate.

9. A compound according to claim 1, which is 2-3,4-dihydroquinolyl(4-(4-(5-methylpyrimidin-2-yl)piperazinyl)butyl)amine fumarate.

10. A compound according to claim 1, which is 2-3,4-dihydroquinolyl(2-(4-(2-pyridyl)piperazinyl)ethyl)amine fumarate.

11. A compound according to claim 1, which is 2-3,4-dihydroquinolyl(3-(4-(2-pyridyl)piperazinyl)propyl)amine fumarate.

12. A compound according to claim 1, which is 2-3,4-dihydroquinolyl(4-(4-(2-pyridyl)piperazinyl)butyl)amine fumarate.

13. A compound according to claim 1, which is 2-3,4-dihydroquinolyl(2-(4-(pyrimidin-2-yl)piperazinyl)ethyl)amine.

14. A compound according to claim 1, which is 2-3,4-dihydroquinolyl(3-(4-(pyrimidin-2-yl)piperazinyl)propyl)amine.

15. A compound according to claim 1, which is 2-3,4-dihydroquinolyl(4-(4-(5-fluoropyrimidin-2-yl)piperazinyl)butyl)amine.

16. A compound according to claim 1, which is 2-3,4-dihydroquinolyl(2-(4-(5-fluoropyrimidin-2-yl)piperazinyl)ethyl)amine.

17. A compound according to claim 1, which is 2-3,4-dihydroquinolyl(3-(4-(5-fluoropyrimidin-2-yl)piperazinyl)propyl)amine.

18. A compound according to claim 1, which is 2-3,4-dihydroquinolyl(4-(4-(5-fluoropyrimidin-2-yl)piperazinyl)butyl)amine.

19. A compound according to claim 1, which is 2-3,4-dihydroquinolyl(4-(4-(5-methylpyrimidin-2-yl)piperazinyl)butyl)amine.

20. A compound according to claim 1, which is 2-3,4-dihydroquinolyl(2-(4-(2-pyridyl)piperazinyl)ethyl)amine.

21. A compound according to claim 1, which is 2-3,4-dihydroquinolyl(3-(4-(2-pyridyl)piperazinyl)propyl)amine.

22. A compound according to claim 1, which is 2-3,4-dihydroquinolyl(4-(4-(2-pyridyl)piperazinyl)butyl)amine.

* * * * *